US011612429B2

(12) United States Patent
Brannan et al.

(10) Patent No.: US 11,612,429 B2
(45) Date of Patent: *Mar. 28, 2023

(54) SYSTEMS AND METHODS FOR THERMAL ABLATION DISTORTION DETECTION

(71) Applicant: Covidien LP, Mansfield, MA (US)

(72) Inventors: Joseph D. Brannan, Erie, CO (US); Anthony B. Ross, Boulder, CO (US); Casey M. Ladtkow, Erie, CO (US)

(73) Assignee: Covidien LP, Mansfield, MA (US)

( * ) Notice: Subject to any disclaimer, the term of this patent is extended or adjusted under 35 U.S.C. 154(b) by 1337 days.

This patent is subject to a terminal disclaimer.

(21) Appl. No.: 15/995,037

(22) Filed: May 31, 2018

(65) Prior Publication Data

US 2018/0344390 A1 Dec. 6, 2018

Related U.S. Application Data

(60) Provisional application No. 62/512,984, filed on May 31, 2017.

(51) Int. Cl.
*A61B 18/14* (2006.01)
*A61B 18/12* (2006.01)
(Continued)

(52) U.S. Cl.
CPC ...... *A61B 18/1477* (2013.01); *A61B 18/1206* (2013.01); *A61B 18/148* (2013.01);
(Continued)

(58) Field of Classification Search
CPC .. A61B 2018/0005; A61B 2018/00011; A61B 2018/00577; A61B 2018/00642;
(Continued)

(56) References Cited

U.S. PATENT DOCUMENTS 11,350,984 B2 * 6/2022 Brannan .............. A61B 18/148
2005/0171526 A1 * 8/2005 Rioux ................. C04B 38/0067
606/41

(Continued)

FOREIGN PATENT DOCUMENTS

| CN | 105682589 A | 6/2016 |
| EP | 2361583 A1 | 8/2011 |
| JP | 2017506943 A | 3/2017 |

OTHER PUBLICATIONS

International Search Report and Written Opinion issued in corresponding Appl No. PCT/US2018/035491, dated Sep. 11, 2018 (16 pages).

(Continued)

*Primary Examiner* — Ronald Hupczey, Jr.
*Assistant Examiner* — Bradford C. Blaise
(74) *Attorney, Agent, or Firm* — Carter, DeLuca & Farrell LLP

(57) ABSTRACT

Ablation systems and methods detect and address distortion caused by a variety of factors. A method includes measuring a temperature curve at target tissue; applying ablation energy to the target tissue; determining a peak temperature on the temperature curve; if the peak temperature is greater than the predetermined peak temperature, determining a time at which the temperature curve crosses to a lower temperature; and if the determined time is greater than a predetermined time, generating a message indicating that the target tissue was successfully ablated. Another method includes determining a distance between a remote temperature probe and an ablation probe, applying ablation energy to target tissue, measuring temperature at the remote temperature probe, estimating ablation size based on the determined distance and the temperature measured by the remote temperature (Continued)

probe, and determining whether the target tissue is successfully ablated based on the estimated ablation size.

18 Claims, 14 Drawing Sheets

(51) Int. Cl.
*A61B 18/00* (2006.01)
*A61B 90/00* (2016.01)
*A61M 5/158* (2006.01)

(52) U.S. Cl.
CPC ........... *A61B 2018/00005* (2013.01); *A61B 2018/00023* (2013.01); *A61B 2018/00029* (2013.01); *A61B 2018/00041* (2013.01); *A61B 2018/00434* (2013.01); *A61B 2018/00577* (2013.01); *A61B 2018/00642* (2013.01); *A61B 2018/00672* (2013.01); *A61B 2018/00678* (2013.01); *A61B 2018/00702* (2013.01); *A61B 2018/00738* (2013.01); *A61B 2018/00761* (2013.01); *A61B 2018/00791* (2013.01); *A61B 2018/00797* (2013.01); *A61B 2018/00821* (2013.01); *A61B 2018/00875* (2013.01); *A61B 2018/00886* (2013.01); *A61B 2018/126* (2013.01); *A61B 2018/1253* (2013.01); *A61B 2018/1266* (2013.01); *A61B 2018/1425* (2013.01); *A61B 2090/061* (2016.02); *A61M 5/158* (2013.01)

(58) Field of Classification Search
CPC ........... A61B 2018/00666; A61B 2018/00672; A61B 2018/00678; A61B 2018/00702; A61B 2018/00714; A61B 2018/00761; A61B 2018/00791; A61B 2018/00797; A61B 2018/00803; A61B 2018/00815; A61B 2018/00821; A61B 2018/00875; A61B 18/1206; A61B 18/1477; A61B 18/148

See application file for complete search history.

(56) References Cited

U.S. PATENT DOCUMENTS

| | | |
|---|---|---|
| 2006/0106375 A1 | 5/2006 | Werneth et al. |
| 2007/0135811 A1 | 6/2007 | Hooven |
| 2011/0082351 A1* | 4/2011 | Razzaque ............ A61B 5/744 600/301 |
| 2011/0208180 A1 | 8/2011 | Brannan |
| 2012/0239030 A1* | 9/2012 | Ladtkow ............ A61B 18/1206 606/41 |
| 2014/0330266 A1* | 11/2014 | Thompson ......... A61B 18/1206 606/34 |
| 2015/0105765 A1* | 4/2015 | Panescu ................ A61B 18/12 606/34 |
| 2016/0278856 A1 | 9/2016 | Panescu et al. |
| 2016/0317218 A1* | 11/2016 | Sigmon, Jr. ......... A61B 18/1477 |
| 2016/0324575 A1 | 11/2016 | Panescu et al. |

OTHER PUBLICATIONS

Chinese Office Action issued in corresponding application CN 201880035633.2 dated Sep. 13, 2022, including English language translation (11 pages).

* cited by examiner

SYSTEMS AND METHODS FOR THERMAL ABLATION DISTORTION DETECTION

BACKGROUND

RF (radio frequency) ablation is used in a variety of ablative treatment applications. For example, RF is used to perform surgery on vertebral bodies and to perform nerve ablation. Nerve ablation is performed near the facet joint in the spine. The facet joints are synovial, plane joints between the articular processes of two adjacent vertebrae. Each facet joint is innervated by the recurrent meningeal nerves. In general, the desired outcome of a nerve ablation procedure is to fully denervate the innervation of the facet joint, which may provide 12 to 24 months of pain relief. In some cases, however, it may take four to six weeks to confirm a successful nerve ablation procedure.

SUMMARY

In one aspect, this disclosure features a method for determining whether target tissue was successfully ablated. The method includes applying ablation energy to target tissue; measuring a temperature curve at the target tissue; determining a peak temperature on the temperature curve; determining whether the peak temperature is greater than a predetermined peak temperature; if the peak temperature is greater than the predetermined peak temperature, determining a time at which the temperature curve crosses to a temperature lower than the predetermined peak temperature; and if the determined time is greater than a predetermined time, generating a message indicating that the target tissue was successfully ablated.

In aspects, the predetermined peak temperature and the predetermined time are based on the symmetric ablation of tissue similar to the target tissue.

In aspects, the method includes, if the peak temperature is not greater than the predetermined peak temperature or if the determined time is not greater than a predetermined time, generating a message indicating that the target tissue was not properly ablated.

In aspects, measurement of the temperature curve is performed by a thermocouple or temperature sensor disposed on or within an ablation electrode.

In aspects, measurement of the temperature curve is performed by one or more temperature probes remote from an ablation electrode.

In aspects, the method includes measuring the temperature curve at a plurality of locations in the target tissue.

In aspects, the method includes applying a small amount of energy to the target tissue in a pre-heat stage, measuring a temperature curve in the pre-heat stage, and determining an amount of ablation energy to apply to the target tissue based on the temperature curve.

In aspects, the method includes determining a rate of change of at least a portion of the temperature curve, and determining the amount of ablation energy based on the rate of change of at least a portion of the temperature curve.

In aspects, the method includes cooling the target tissue in a pre-heat stage, measuring a temperature curve in the pre-heat stage, and determining an amount of ablation energy to apply to the target tissue based on the temperature curve.

In aspects, the method includes determining a rate of change of at least a portion of the temperature curve, and determining the amount of ablation energy based on the rate of change of at least the portion of the temperature curve.

In another aspect, this disclosure features a system for determining whether target tissue was successfully ablated. The system includes a radio frequency (RF) generator configured to generate RF energy, an ablation electrode configured to deliver RF energy to target tissue to ablate the target tissue, a temperature sensor configured to measure temperature at the target tissue, and a controller. The controller is configured to: control the temperature sensor to measure a temperature curve at the target tissue; control the RF generator to supply RF energy to the ablation electrode; determine a peak temperature on the temperature curve; determine whether the peak temperature is greater than a predetermined peak temperature; if the peak temperature is greater than the predetermined peak temperature, determine a time at which the temperature curve crosses to a temperature lower than the predetermined peak temperature; and if the determined time is greater than a predetermined time, issue generating a message indicating that the target tissue was successfully ablated.

In aspects, the controller includes a processor and a memory having stored thereon instructions, which, when executed by the processor, cause the processor to perform the functions of the controller.

In aspects, the temperature sensor is disposed on or within the ablation electrode.

In aspects, the temperature sensor is disposed on or within a remote temperature probe.

In aspects the temperature sensor is a first temperature sensor, the system includes a second temperature sensor disposed on or within a remote temperature probe, and the first and second temperature sensors are configured to measure the temperature curve at the target tissue.

In aspects, the temperature sensor is a thermocouple.

In aspects, the controller is configured to: cool the target tissue in a pre-heat stage, measure a temperature curve in the pre-heat stage, and determine an amount of RF energy to apply to the target tissue based on the temperature curve.

In aspects, the controller is configured to: determine a rate of change of at least a portion of the temperature curve and determine the amount of ablation energy based on the rate of change of at least a portion of the temperature curve.

In aspects, the controller is further configured to: cool the target tissue in a pre-cooling heat stage, measure a temperature curve in the pre-cooling heat stage, and determine an amount of ablation energy to apply to the target tissue based on the temperature curve.

In aspects, the controller is configured to: determine a rate of change of at least a portion of the temperature curve, and determine the amount of ablation energy based on the rate of change of at least the portion of the temperature curve.

In yet another aspect, this disclosure features a method of estimating ablation size. The method includes determining a distance between a remote temperature probe and an ablation probe, applying ablation energy to target tissue, measuring temperature at the remote temperature probe, and estimating ablation size based on the determined distance and the temperature measured by the remote temperature probe.

In aspects, the method includes determining whether the target tissue is successfully ablated based on the estimated ablation size.

In aspects, determining whether the target tissue is successfully ablated includes determining whether the estimated ablation size includes the target tissue.

In aspects, the target tissue is a nerve or a tumor.

In aspects, the determined distance is between about 1.0 cm and about 2.0 cm.

In aspects, estimating ablation size includes: interpolating between the measured temperature, an assumed temperature near the ablation electrode, and an assumed initial temperature remote from the ablation electrode to obtain temperature values; evaluating the Arrhenius integral equation using the obtained temperature values; and determining ablation size based on the result of evaluating the Arrhenius integral equation.

In aspects, interpolating is performed using a logarithmic decay function.

In yet another aspect, this disclosure features a system for estimating ablation size. The system includes a radio frequency (RF) generator configured to generate RF energy, an ablation electrode configured to deliver RF energy to target tissue to ablate the target tissue, a remote temperature probe configured to measure temperature at the target tissue, and a controller. The controller is configured to: determine a distance between a remote temperature probe and an ablation probe, control the RF generator to provide RF energy to the ablation electrode, measure temperature at the remote temperature probe, and estimate ablation size based on the determined distance and the temperature measured by the remote temperature probe.

In aspects, the controller is configured to determine whether the target tissue is successfully ablated based on the estimated ablation size.

In aspects, determining whether the target tissue is successfully ablated includes determining whether the estimated ablation size includes the target tissue.

In aspects, the target tissue is a nerve or a tumor.

In aspects, the determined distance is between about 1.0 cm and about 2.0 cm.

In aspects, estimating ablation size comprises: interpolating between the measured temperature, an assumed temperature near the ablation electrode, and an assumed initial temperature remote from the ablation electrode to obtain temperature values; evaluating the Arrhenius integral equation using the obtained temperature values; and determining ablation size based on the result of evaluating the Arrhenius integral equation.

In aspects, the interpolating is performed using a logarithmic decay function.

In yet another aspect, this disclosure features a method of ablating a nerve. The method includes inserting a needle at probable location of nerve, delivering a diagnostic block through the needle, removing the needle, determining whether the diagnostic effectively blocks the nerve, if the diagnostic block effectively blocks the nerve, inserting an ablation probe at the location where the needle was inserted, and applying RF energy to the nerve through the inserted ablation probe to ablate the nerve.

In aspects, the method includes, if the diagnostic block does not effectively block the nerve, inserting the needle at another probable location of the nerve.

In aspects, delivering the diagnostic block includes delivering a sufficient amount of diagnostic block to effectively block the nerve but delivering less than an amount needed to accurately locate the nerve.

In aspects, the diagnostic block is an anesthetic, a fast-acting anesthetic, or lidocaine.

In yet another aspect, this disclosure features another method for determining whether target tissue is successfully ablated. The method includes applying, by an ablation electrode, ablation energy at target tissue, cooling the ablation electrode, measuring a temperature curve at the target tissue, determining whether the ablation procedure was successful based on the temperature curve, and, if it is determined that the ablation procedure was successful, issuing a message indicating that the target tissue was successfully ablated.

In aspects, the method includes, if it is determined that the ablation procedure was not successful, issuing a message indicating that the target tissue was not successfully ablated.

In yet another aspect, this disclosure features another system for determining whether an ablation procedure is successful. The system includes a radio frequency (RF) generator configured to generate RF energy, an ablation electrode configured to deliver RF energy to target tissue to ablate the target tissue, a cooling fluid pump configured to pump cooling fluid to the ablation electrode, a temperature sensor configured to measure temperature at the target tissue, and a controller. The controller is configured to: control the RF generator to supply RF energy to an the ablation electrode, control the cooling fluid pump to pump cooling fluid to the ablation electrode, measure a temperature curve at the target tissue, determine whether the ablation procedure was successful based on the temperature curve, and, if it is determined that the ablation procedure was successful, issuing a message indicating that the target tissue was successfully ablated.

In aspects, the remote temperature probe includes a thermocouple.

In aspects, the controller is configured to, if it is determined that the ablation procedure was not successful, issue a message indicating that the target tissue was not successfully ablated.

In aspects, the controller includes a processor and a memory having stored thereon instructions, which, when executed by the processor, cause the processor to perform the functions of the controller.

In aspects, the remote temperature probe is a first remote temperature probe, the system includes a second remote temperature probe, and the first and second temperature probes are configured to measure the temperature curve at the target tissue.

BRIEF DESCRIPTION OF THE DRAWINGS

Various aspects of this disclosure are described below with reference to the drawings, wherein.

DETAILED DESCRIPTION

This disclosure relates to ablation systems and methods for detecting and addressing distortion, which may be caused by a variety of factors including the distortion caused by local anatomy. This disclosure also features systems and methods for determining whether an ablation procedure, e.g., to ablate nerves, is successful.

Figure 1A:
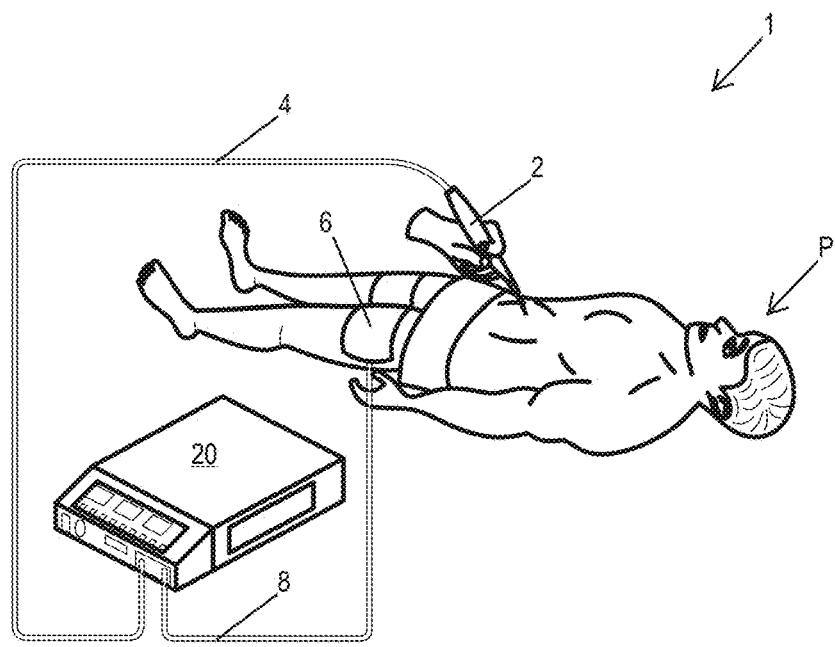
FIG. 1A is a block diagram of an RF ablation system being used to treat a patient according to embodiments of this disclosure.

FIG. 1A is an illustration of a monopolar RF system 1 according to one embodiment. The system 1 includes an ablation instrument 2 having one or more electrodes for treating tissue, e.g., nerves, of a patient P. The instrument 2 is a monopolar-type instrument including one or more active ablation electrodes. RF energy is supplied to the instrument 2 by an RF generator 20 via an supply line 4, which is connected to an active terminal 30 (FIG. 1B) of the RF generator 20, allowing the instrument 2 to ablate and/or otherwise treat tissue. The RF energy is returned to the RF generator 20 through a return electrode 6 via a return line 8 at a return terminal 32 (FIG. 1B) of the RF generator 20. The active terminal 30 and the return terminal 32 are connectors configured to interface with plugs (not explicitly shown) of the instrument 2 and the return electrode 6, respectively, which are disposed at the ends of the supply line 4 and the return line 8.

The system 1 may include a plurality of return electrodes 6 that are arranged to minimize the chances of tissue damage by maximizing the overall contact area with the patient P. In addition, the RF generator 20 and the return electrode 6 may be configured for monitoring so-called "tissue-to-patient" contact to insure that sufficient contact exists therebetween to further minimize chances of tissue damage.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment success indicators, etc.). The controls allow the user to adjust power of the RF energy, waveform, and other parameters to achieve the desired waveform suitable for a particular task (e.g., ablating nerves, intensity setting, etc.). The instrument 2 may also include a plurality of input controls that may be redundant with certain input controls of the generator 20. Placing the input controls at the instrument 2 allows for easier and faster modification of RF energy parameters during the ablation procedure without requiring interaction with the generator 20.

Figure 1B:
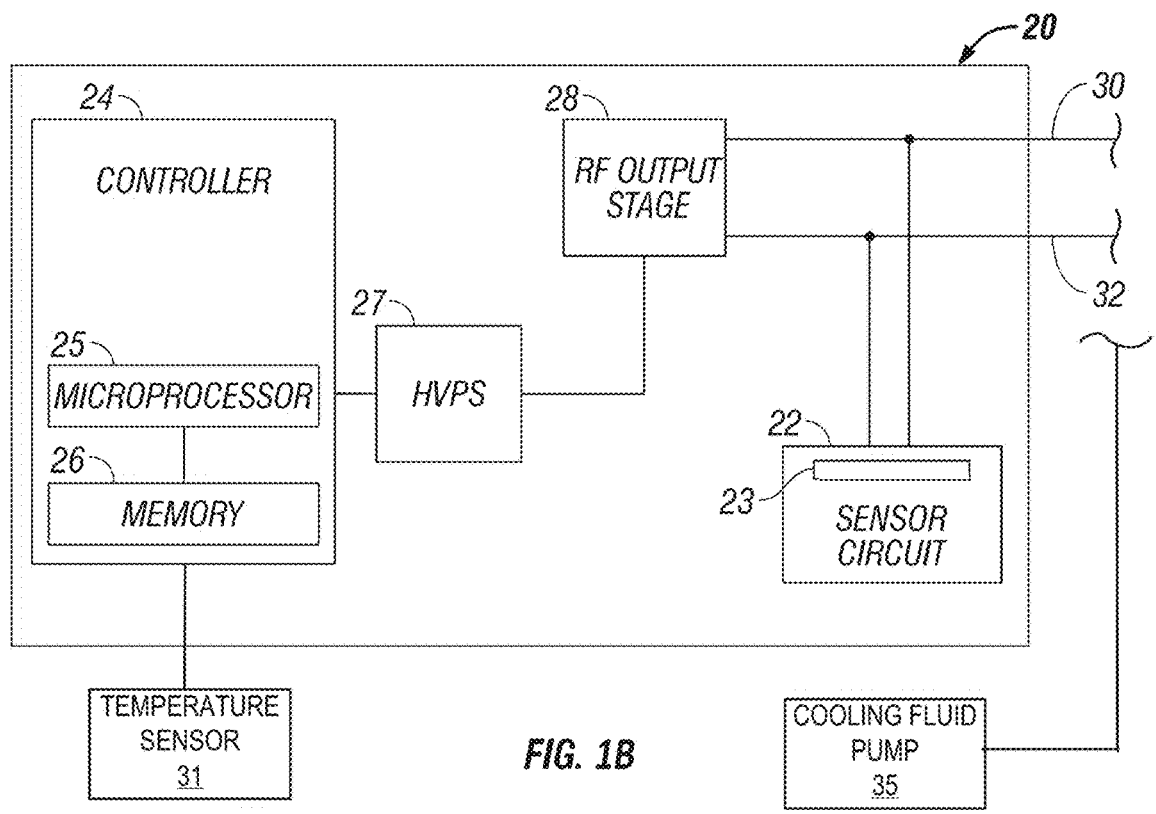
FIG. 1B is a schematic block diagram of an RF ablation system including the RF generator of FIG. 1A.

FIG. 1B is a schematic block diagram illustrating an ablation system according to one embodiment of this disclosure. The generator 20 includes a controller 24, a high voltage DC power supply 27 (HVPS), and an RF output stage 28. The controller 24 includes a power supply (not shown), for example, a low voltage DC power supply, which provides low voltage power to circuitry of the controller 24 and/or RF output stage 28. The HVPS 27 is connected to a conventional AC source (e.g., electrical wall outlet) and provides high voltage DC power to an RF output stage 28, which then converts high voltage DC power into RF energy and delivers the RF energy to the active terminal 30. The energy is returned to the RF output stage 28 via the return terminal 32.

In particular, the RF output stage 28 generates sinusoidal waveforms of high RF energy. The RF output stage 28 is configured to generate a plurality of waveforms having various duty cycles, peak voltages, crest factors, and other suitable parameters. Certain types of waveforms are suitable for specific electrosurgical modes. For instance, the RF output stage 28 generates a 100% duty cycle sinusoidal waveform in cut mode, which is best suited for ablating, fusing, and dissecting tissue, and a 1-25% duty cycle waveform in coagulation mode, which is best used for cauterizing tissue to stop bleeding.

The generator 20 may include a plurality of connectors to accommodate various types of instruments (e.g., monopolar instrument 2, bipolar instrument, etc.). Further, the generator 20 is configured to operate in a variety of modes such as monopolar ablation, bipolar ablation, etc. It is envisioned that the generator 20 may include a switching mechanism (e.g., relays) to switch the supply of RF energy between the connectors, such that, for instance, when the instrument 2 is connected to the generator 20, only the monopolar plug receives RF energy.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., a digital signal processor or a field programmable gate array) adapted to perform the methods described herein. In embodiments, some of the functions or the combination of functions described below may be embodied in program code or a software application, which is stored in the memory 26 and which may be executed by the microprocessor 25.

A closed loop control scheme is a feedback control loop wherein sensor circuit 22 and/or crest factor detection circuit 23, which both may include a plurality of sensors measuring a variety of tissue and energy properties provide feedback to the controller 24. Such sensors are within the purview of those skilled in the art. The controller 24 then signals the HVPS 27 and/or RF output stage 28, which then adjust DC and/or RF power supply, respectively. The controller 24 also receives input signals from the input controls of the generator 20 or the instrument 2. The controller 24 utilizes the input signals to adjust power outputted by the generator 20 and/or performs other control functions thereon.

A temperature sensor 31, which may be disposed on or within the ablation probe or a remote temperature probe, is coupled to the controller 24 of the generator 20 so as to communicate temperature data to the controller 24, which processes the temperature data as described herein. The ablation system may also include a cooling fluid pump 35 for pumping cooling fluid to the ablation instrument 2. In embodiments, the cooling fluid may be circulated through the ablation instrument 2 to cool the surrounding tissue so that a cooling profile may be obtained and used to determine the success or failure of an ablation procedure.

Figure 1C:
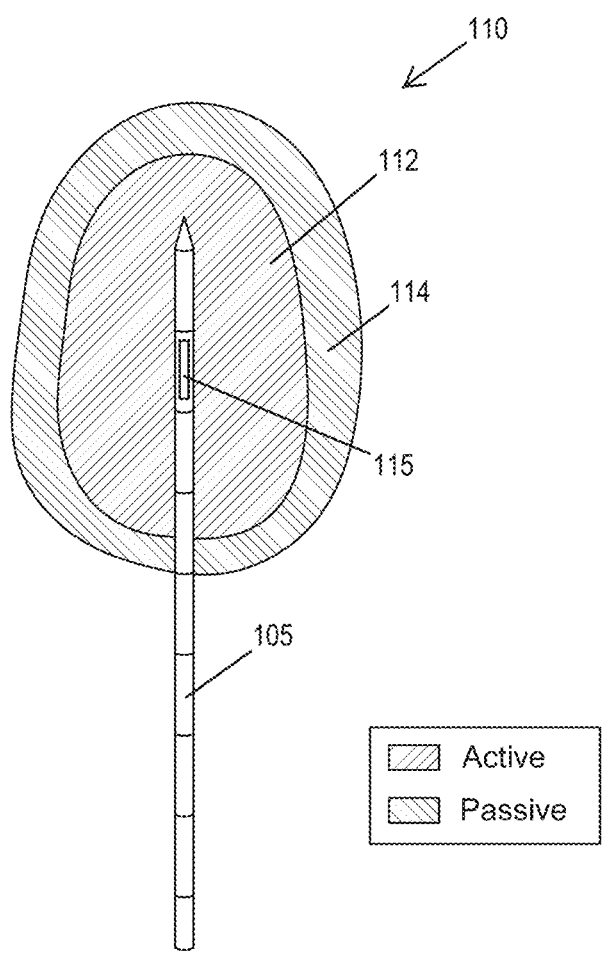
FIG. 1C is a diagram illustrating a heating profile around an RF electrode of the ablation instrument of FIG. 1A.
Figure 2:
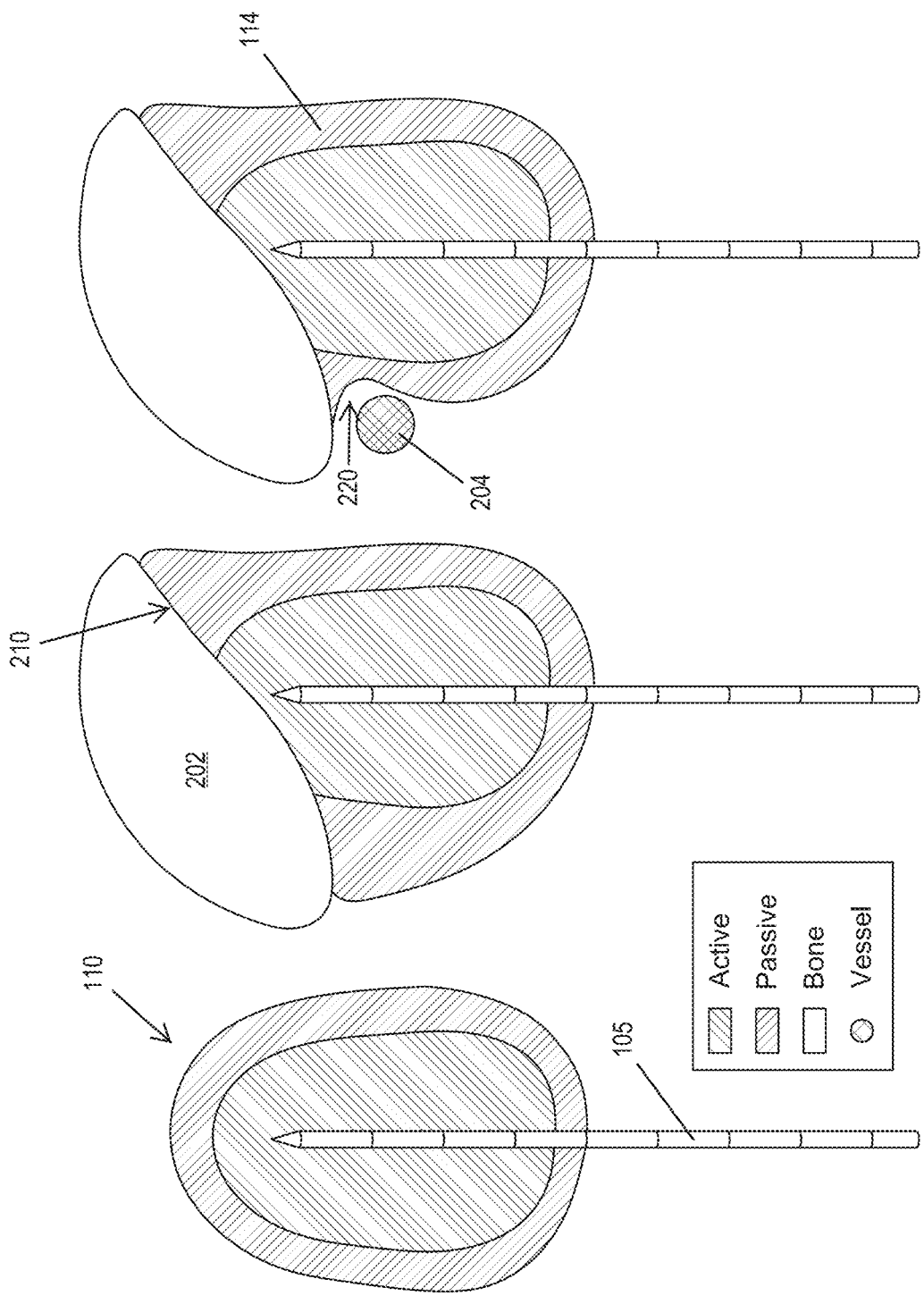
FIG. 2 is a diagram illustrating distortion of the passive heating zone around an RF electrode.

In RF ablation, alternating current flows through an ablation electrode, causing ionic agitation, and therefore friction, in nearby tissue. The friction creates heat, which kills the target tissue. The RF ablation forms a heating profile 110 having a shape as shown, for example, in FIG. 1C. The heating profile 110 includes an active heating portion or zone 112 and a passive heating portion or zone 114. In some embodiments, a temperature sensor 115 is disposed or incorporated in the ablation electrode 105, e.g., in the tip of the ablation electrode, to measure and/or estimate the temperature of the heating profile 110. Ideally, the heating profile is symmetric around the electrode 105. However, the passive heating zone 114 around the ablation electrode 105 can be distorted by anatomical factors including perfusion rates of local anatomy, as illustrated by FIG. 2. For example, around bones 202 there may be some enhanced passive heating, which may spread along a boundary 210. Also, as illustrated in FIG. 2, large vessels 204 or micro-vessels mediate passive heating so that the passive heating zone 114 of the heating profile shrinks or becomes distorted (220), or passive heating is prevented in certain areas.

Figure 3A:
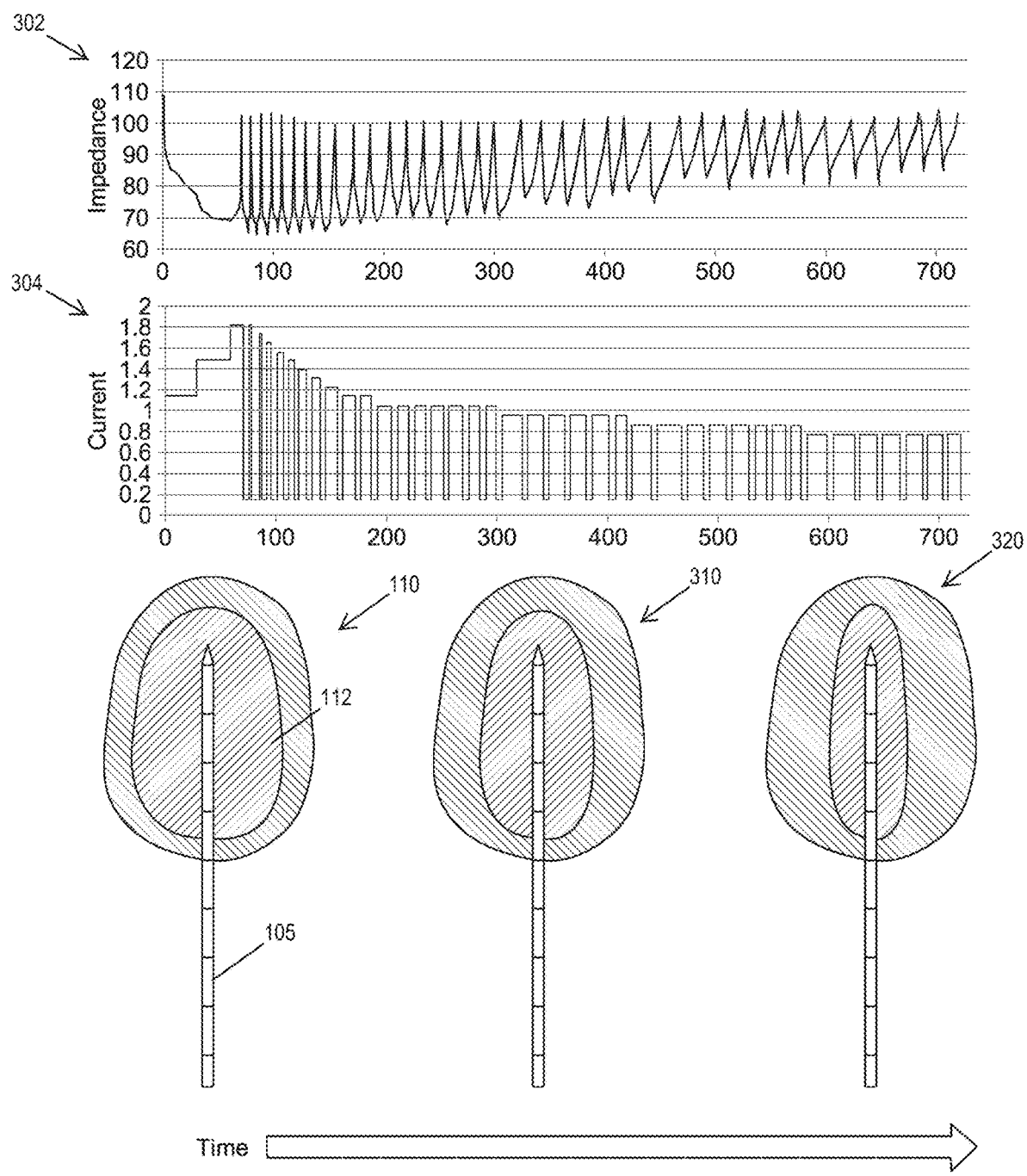
FIGS. 3A and 3B are diagrams illustrating the distortion of heating profiles around an RF electrode.
Figure 3B:
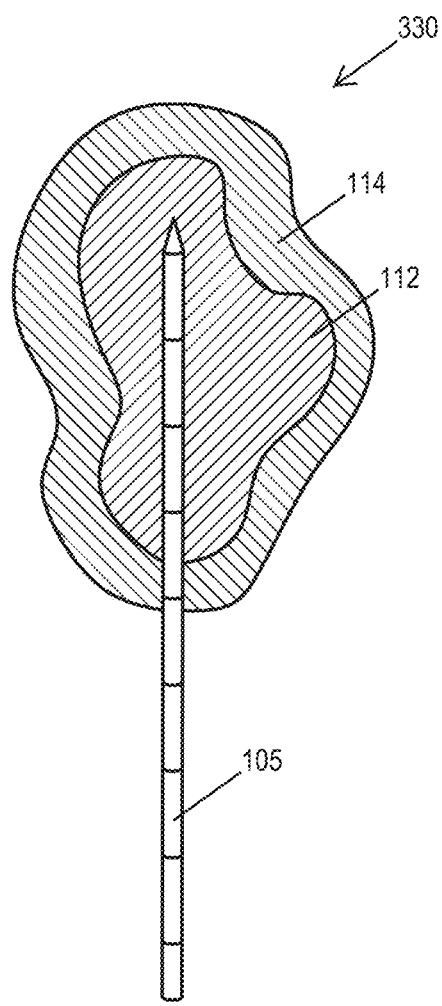

As illustrated in FIG. 3A, in the active heating zone 112, there is a challenge with RF energy where the heating or energy profile shrinks over time (from heating profile 110 to heating profile 310 to heating profile 320) as the ablation desiccates tissue and the impedance shown in graph 302 increases (thus decreasing current flow as shown in graph 304). In some cases, the RF energy spreads symmetrically from the ablation electrode 105, as illustrated in the state 110; but, in other cases, the RF energy may get pulled into an asymmetric pattern 330 in the cross axis of the ablation electrode 105 by anatomical energy sinks or as a result of variations in anatomical conductivity, as illustrated in FIG. 3B.

Figures 4A, 4B, 4C, 4D:
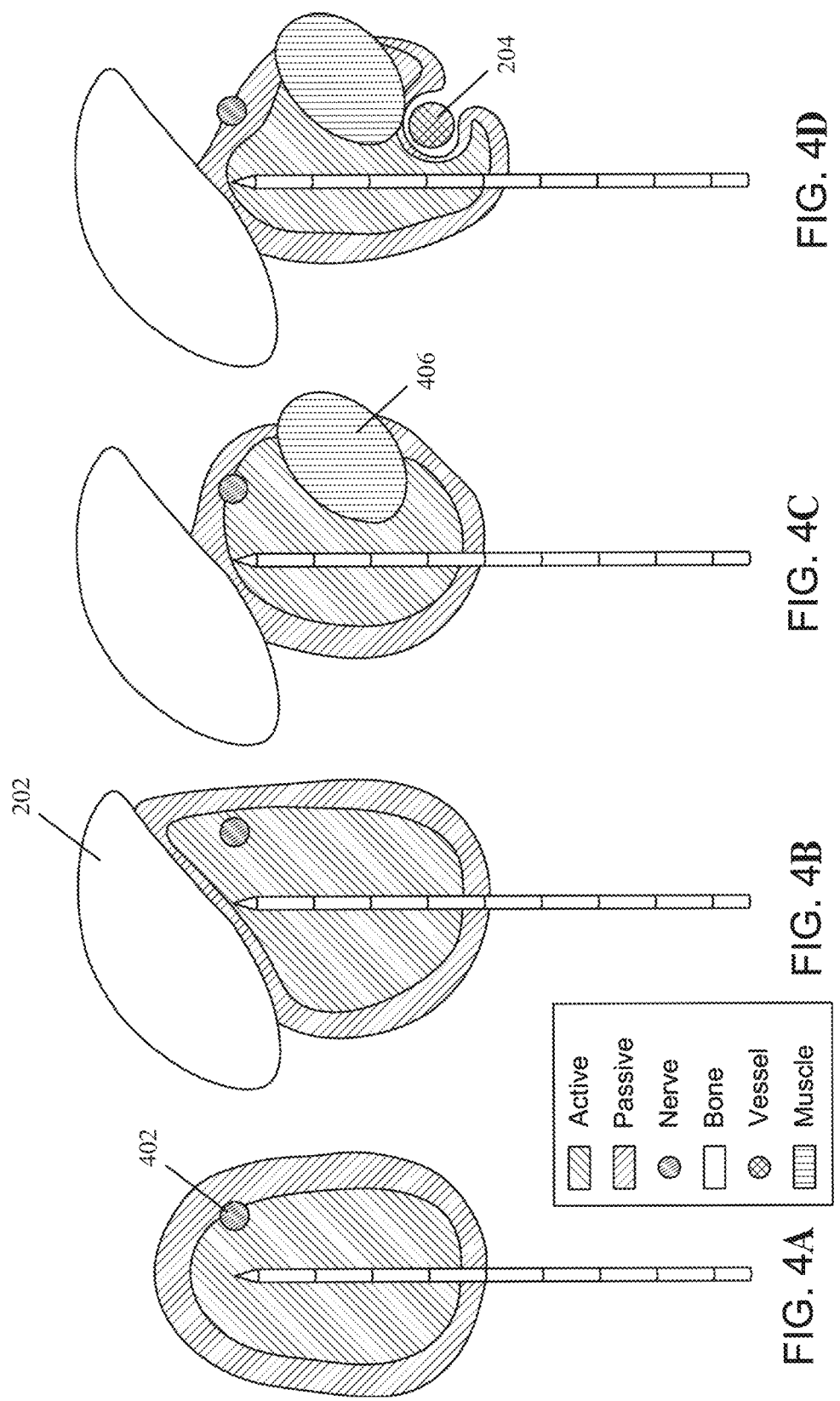
FIGS. 4A-4D are graphical diagrams illustrating distortion of heating profiles around an RF electrode and its effect on nerve ablation.

As illustrated in FIGS. 4A-4D, the shape of the heating profile may be asymmetric due to variations in anatomical conductivity. As illustrated in FIG. 4B, bone 202 is less conductive and thus pushes energy away. As illustrated in FIG. 4C, muscle 406 is more conductive and thus pulls energy towards the muscle 406. And, as illustrated in FIG. 4C, blood vessels 204 are like wires connecting to a ground path so that the blood vessels 204 pull energy towards them, which means that energy is pulled away from other areas. If RF energy is delivered for a long enough period, the impedance problems self-heal because the RF energy is impeded out in areas where the energy is going, but the RF energy starts going other places. In RF nerve ablation, the RF energy is applied to a nerve, for example, for about a minute with less power. The effects of anatomical conductivity described above are accentuated for shorter times and lower powers before impedance walls start building around the ablation electrode 105.

Figure 5:
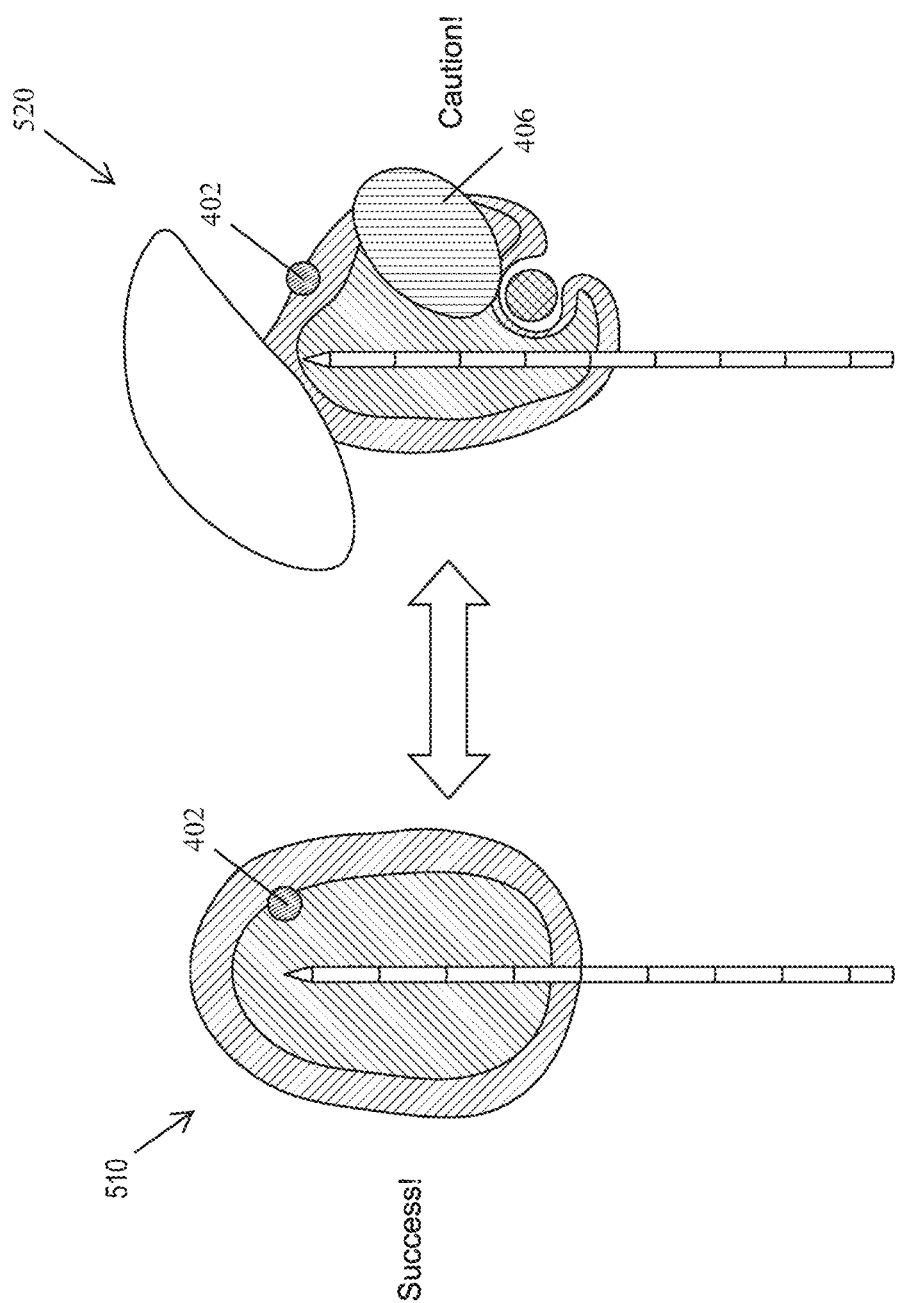
FIG. 5 is a diagram illustrating a symmetric heating profile that results in successful ablation of the target tissue and a distorted heating profile that results in an unsuccessful ablation of the target tissue.

Two-dimensional (2D) heating profiles, e.g., the heating profiles of FIGS. 4A-4D, may be predicted according to embodiments of this disclosure to determine whether target tissue is properly heated. The challenge is differentiating the two heating profiles 510, 520 of FIG. 5. In heating profile 520, the nerve 402 may not be properly ablated. When the ablation electrode 105 is placed in tissue to ablate a nerve 402, the surgeon or clinician would like to know whether she is properly ablating the nerve 402. If the RF energy is close enough to the nerve 402 and the heating profile is symmetrical, as illustrated by the heating profile 510, or is nearly symmetrical, the nerve 402 may be successfully ablated. But if the RF energy is close enough to the nerve 402 and the heating profile is distorted, as shown in the heating profile 520, the nerve 402 may not be successfully ablated and the surgeon should use caution so as not to harm tissue, e.g., the muscle 406, near the ablation electrode.

In embodiments, the ability to determine whether there is a successful ablation may be improved by looking at the temperature decay measured by temperature sensors. In embodiments, the ablation electrodes 105 may be equipped with thermocouples. If the temperature decay indicates a symmetric thermal pattern around the ablation electrode 105, then there is a greater likelihood of a success condition, e.g., ablating a nerve 402. If the temperature decay indicates a loss in symmetry, there is less likelihood of a successful ablation.

Figure 6A:
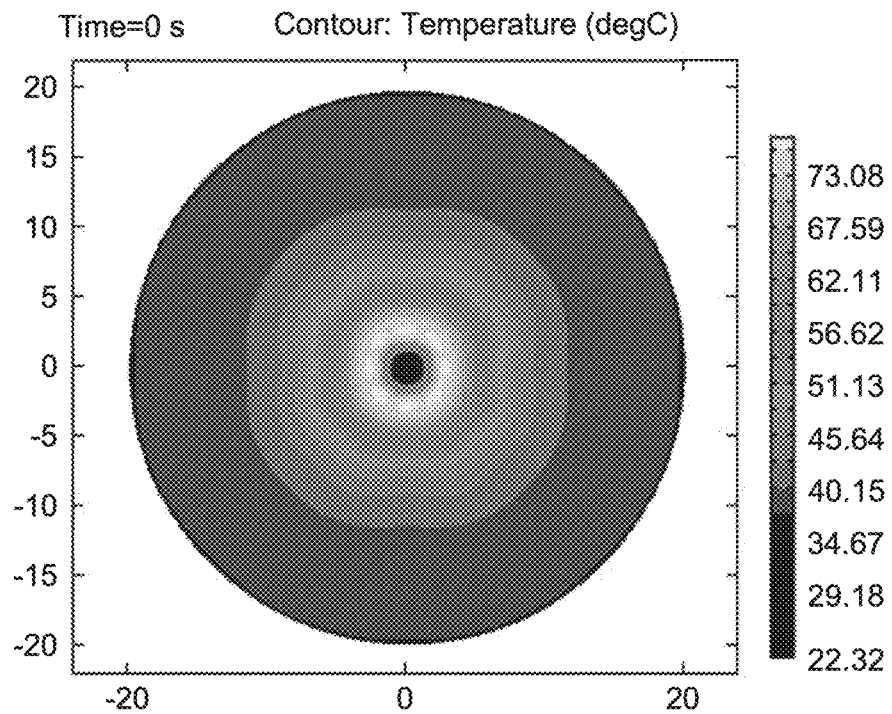
FIG. 6A is an axial view of a heating profile that is symmetric about an RF electrode.
Figure 6B:
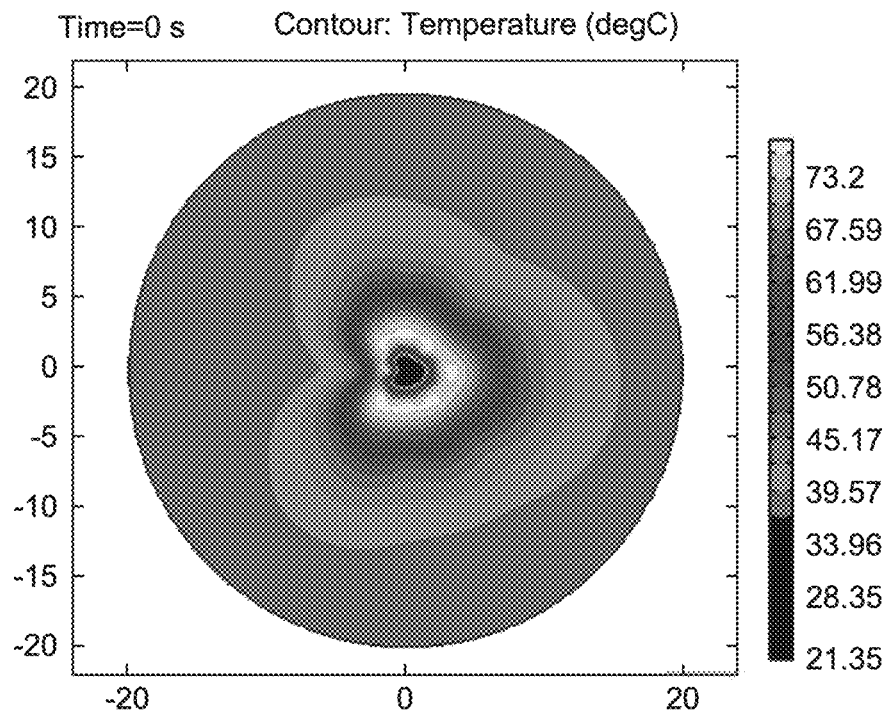
FIG. 6B is an axial view of a heating profile that is distorted.

FIGS. 6A and 6B show models of temperature decay around an ablation electrode. The target tissue may be ablated until a peak temperature is reached and then the peak temperature may be held. The distortion introduces a different crossover point. Thus, with a thermal sink or a thermal mass, the crossover point may be delayed. The methods of this disclosure may determine a peak temperature and a crossover point in a temperature curve to determine whether the target tissue is properly ablated.

The graphical diagrams of FIGS. 6A and 6B show the probe temperature after the RF energy is turned off. In some embodiments, the ablation probe may be cooled. When the RF energy is turned off, the cooling of the electrode is turned off as well. Then, the method includes monitoring how the probe temperatures respond to the ablative mass around the ablation probe 105. The probe temperature curve for symmetric ablation is shown in FIG. 6A. The temperature curve for symmetric ablation has a peak temperature and a crossover point later in time than the probe temperature curve for distorted or asymmetric ablation.

Figure 6C:
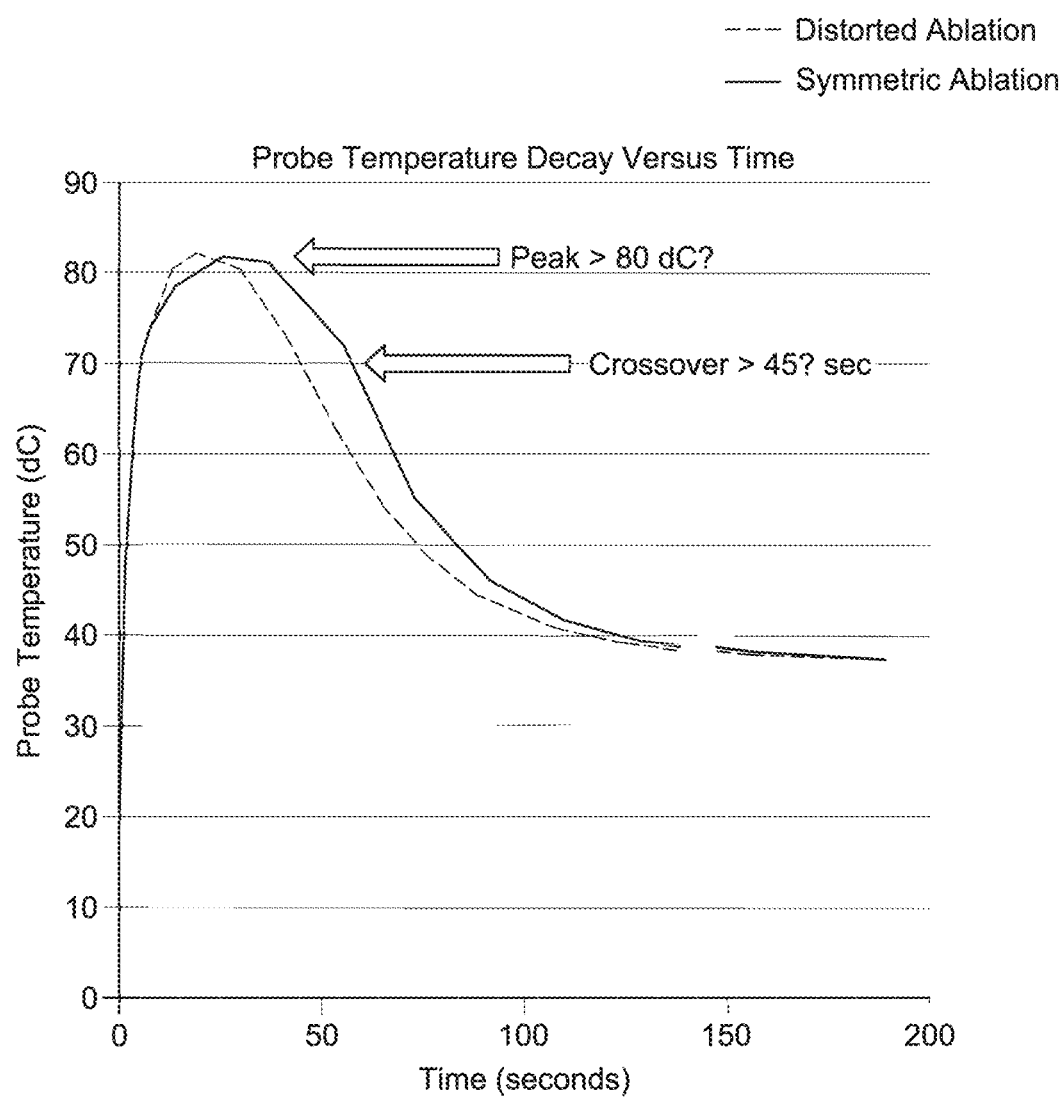
FIG. 6C is a graph illustrating a method of determining whether an ablation was successful.

If the active heating zone misses the ablation target or has an irregular shape, the RF energy is conducted away from the ablation probe in irregular ways. As shown in FIG. 6C, the probe temperature curve decays more quickly in certain places for the distorted ablation. As shown on the left side of FIG. 6B, RF energy quickly conducts away as compared to the right side of FIG. 6B, where the temperature profile is flat. The left side of temperature profile of FIG. 6B is steep. Thus, the heat conducts away from the ablation probe faster on the left side of the temperature profile of FIG. 6B than on the right side of the temperature profile. Thus, the temperature profile of FIG. 6B would have a steeper temperature decay curve and earlier crossover point as shown in FIG. 6C. On the other hand, the temperature profile shown in FIG. 6A shows the heat conducting away from the ablation probe more evenly. For the temperature profile of FIG. 6A, if the ablation probe is in a passive state, the crossover point is later as shown in FIG. 6C

In embodiments, there may be a single thermocouple incorporated in or on the ablation probe or there may be multiple thermocouples incorporated in or on the ablation probe to be able to map the temperature pattern or profile around the ablation probe. In the embodiment of FIG. 1C, the ablation probe 105 includes one thermocouple.

In embodiments, one or more temperature probes, which include thermocouples or temperature sensors, may be used together with the ablation probe having the thermocouple. The one or more temperature probes may be placed a certain distance away from the ablation probe and temperature data from the thermocouples or temperature sensors in the one or more temperature probes and the ablation probe may be acquired and used to indicate to the surgeon whether the ablation procedure was successful.

In embodiments, a temperature growth curve may be acquired and used in a manner similar to the temperature decay curves described above. For example, a cold fluid may be run through the ablation probe or another probe and temperature probes would sense how quickly the temperature of the tissue heats up. In embodiments, the cooling of the ablation probe may be performed in a pre-cooling stage before any RF energy is turned on. The pre-cooling stage would involve cooling the ablation probe and monitoring how fast the temperature increases or grows. The result of monitoring how fast the temperature increases could affect the ablation procedure that is performed after the pre-cooling stage. For example, if the ablation probe and/or the tissue heats up quickly, then more RF energy would need to be used to ablate the same amount of target tissue because something is quickly conducting the energy away.

In other embodiments, there may be a post-cooling stage in which a cooling profile is obtained to determine whether the ablation was successful. For example, the controller 24 of FIG. 1B may first control the RF generator 20 to supply RF energy to an ablation electrode to ablate target tissue. Afterwards, the controller 24 controls the cooling fluid pump 35 of FIG. 1B to pump cooling fluid to the ablation electrode, measures a temperature curve at the target tissue using the temperature sensor 31, determines whether the ablation procedure was successful based on the temperature curve, and, if it is determined that the ablation procedure was successful, issues a message indicating that the target tissue was successfully ablated. On the other hand, if it is determined that the ablation procedure was not successful, the controller issues a message indicating that the target tissue was not successfully ablated. The temperature sensor 31 may be substituted by multiple temperature sensors and may be disposed on or within an ablation probe and/or one or more remote temperature probes.

In embodiments, if the rate of change of temperature rises too quickly while delivering RF energy to tissue, there is a high probability that there is some heat sink activity local to the tip of the ablation probe and more RF energy is needed to achieve the same ablation size. In embodiments, a small amount of RF energy may be supplied to the ablation probe to heat the tissue a small amount in a pre-heat stage. For example, instead of supplying RF energy to the ablation probe for a minute, RF energy could be supplied to the ablation probe for five seconds. If the measured temperature curve shows that the temperature dropped at a fast rate, the ablation procedure can be pre-planned so that instead of heating the tissue for a minute, the tissue can be heated for a minute and a half because of the high conductivity tissue around the ablation probe. Thus, in embodiments, the tissue is preheated to determine the conductivity of the ablation zone, and then the tissue may be fully heated based on the determined conductivity of the ablation zone.

The probe temperature decay graph of FIG. 6C roughly indicates whether there is a heat sink in the area in which the ablation probe is placed and thus are at risk of being categorized as a non-symmetric profile. The temperature decay (or growth) curve may indicate that the ablation needle or probe is placed in something that the surgeon did not intend to place it in. For example, patients with chronic back problems may have had may previous surgeries or interventions, which caused a lot of fibrotic scar tissue to develop in an area. If an ablation probe were placed in a scarred-up area and a measured temperature curve showed a rapid rise in temperature, this would indicate that the heat did not spread. As another example, if the temperature curve did not show a roll-off at all, this may indicate that the ablation probe is in cartilage. On the other hand, if there is a quick roll-off of at least a portion of the temperature curve, this may indicate that the ablation probe is near a blood vessel and should be repositioned.

In another embodiment, single point thermometry is used to enhance the ability to predict a successful ablation. In general, it is complicated to know the temperature at any one location in three-dimensional space. However, with a line of trajectory between the ablation probe and the remote thermocouple needle, there is a higher degree of confidence in knowing the thermal profile. Thus, with a remote thermocouple placed with bracketing near the target tissue location and then monitoring a curve fit between the thermal probe in the RF ablation probe and the thermal probe that is remote, there is a higher degree of confidence in the temperature roll-off, which can give better information regarding whether the target tissue, e.g., a nerve, has been properly ablated and killed between the ablation probe and the remote thermocouple needle.

Figure 7A:
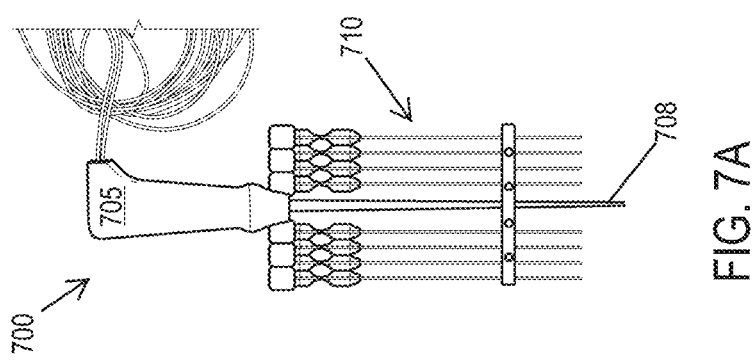
FIG. 7A is a schematic diagram of an ablation assembly used in performing multiple point size estimation.
Figure 7B:
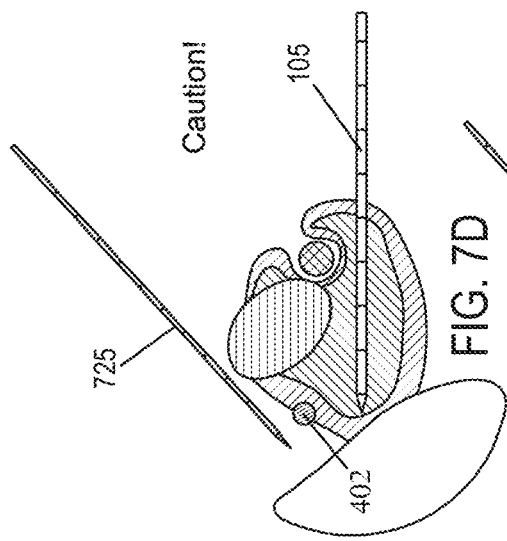
FIG. 7B is a graph illustrating a method for determining ablation size according to an embodiment of this disclosure.

FIGS. 7A and 7B illustrate a multiple point size estimation method or algorithm. FIG. 7A shows an ablation assembly 700 including an ablation instrument 705 and a linear array of cannulae 710, e.g., four cannulae, extending away from the ablation electrode 708 of the ablation instrument 705 in each of two opposite directions. The cannulae 710 are used to introduce temperature probes (not shown) in correct locations. When using eight temperature probes, the size estimation method uses eight total points-four points for each side. The cannulae 710 may be metal cannulae to place the temperature probes, e.g., fiber optic temperature probes. Each cannula may be coated with heat shrink to minimize any affect they may have on the ablation.

In a data collection stage, the temperature probes used in the ablation assembly 700 gather temperature data at known locations with respect to the ablation electrode 708. To increase resolution to achieve an appropriate resolution, interpolation is performed between the temperatures measured at the known locations with respect to the ablation electrode 708. Next, the time integral of the Arrhenius equation is calculated. The Arrhenius integral equation may be expressed as follows:

$$\Omega = -\ln\left(\frac{C(\tau)}{C(0)}\right) = A \int_0^\tau e^{\left(-\frac{E}{RT(t)}\right)} dt \qquad (1)$$

where $\Omega$ represents the damage sustained by the tissue, $C(\tau)/C(0)$ is the ratio of the concentration of the component of interest at time zero to the original concentration, $T(t)$ is the temperature, A is a constant, E is the activation energy required to ensure that the nerve is dead, and R is the universal gas constant. Then, as illustrated in FIG. 7B, the ablation size is determined based on the distance at which $\Omega$ is greater than a predetermined value.

Figure 7C:
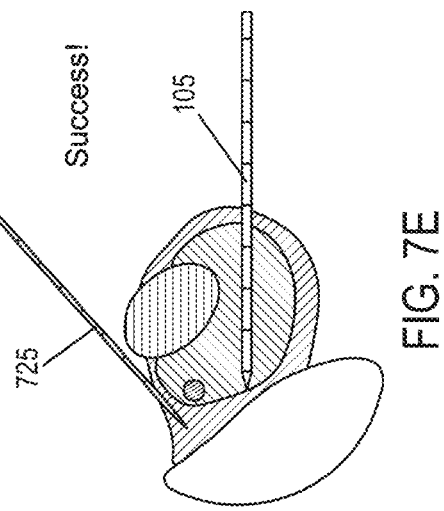
FIG. 7C is a graph illustrating the application of boundary conditions to allow for interpolation according to an embodiments of this disclosure.
Figure 7D:
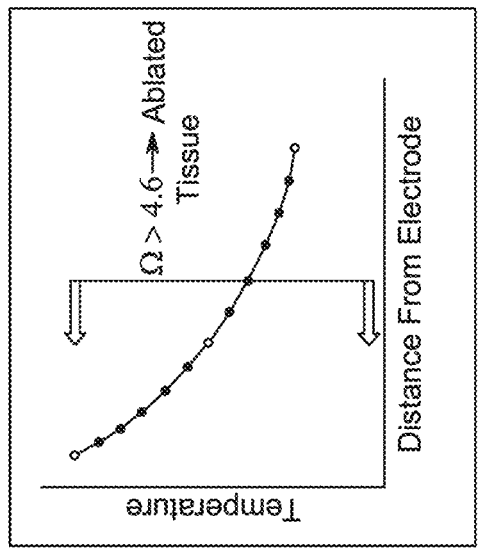
FIG. 7D is a block diagram illustrating unsuccessful ablation of a nerve.
Figure 7E:
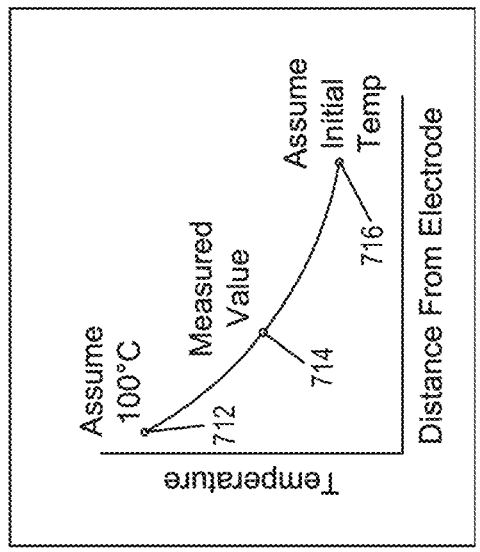
FIG. 7E is a block diagram illustrating successful ablation of a nerve.

The disadvantage of multiple point size estimation is that it requires multiple remote temperature probes. Single point size estimation, however, requires only a single remote temperature probe 725, as illustrated in FIGS. 7D and 7E. Single point size estimation is performed in the same way as multiple point size estimation except that only a single temperature point 714 measured by the remote temperature probe 725 is used to estimate each radius.

To perform single point size estimation, two assumptions are made. As illustrated in the graph of FIG. 7C, the first assumption is that the temperature near the ablation electrode, e.g., approximately 0.5 cm away from the ablation electrode, is 100° C. (point 712). When pulsing RF energy, the temperature is 100° C. approximately 3-5 mm away from the ablation electrode. The other assumption is that the temperature reaches equilibrium (i.e., the normal state of the tissue) at some location far away from the ablation electrode, e.g., initial temperature point 716. In this manner, boundary conditions are added or applied to a single point measured temperature value (point 714) to allow for interpolation. Then, interpolation is performed and the Arrhenius integral equation is calculated and analyzed to determine whether the ablation was unsuccessful as illustrated in FIG. 7D, or whether the ablation was successful as illustrated in FIG. 7E. The analysis may include determining the size of the ablation zone and determining whether the size of the ablation zone is large enough to successfully ablate target tissue.

The interpolation function may be the logarithmic decay function. Any number of temperature values can be interpolated between the measured or known temperature value 714 and the boundary conditions. More interpolated temperature values lead to better resolution, but this may increase calculation time. In some embodiments, a second remote temperature probe may be placed in the tissue to improve resolution.

In embodiments, the surgeon may place the ablation probe, place the temperature probe, e.g., a thermocouple needle, measure the distance between the ablation probe and the thermocouple, and confirm that the nerve is in between the ablation probe and the thermocouple. The surgeon may then enter the measured distance into a user interface. The surgeon may then run a software application to monitor the temperature of the temperature probe and the temperature of the ablation electrode. The software application may also monitor the power of the RF energy delivered to the target tissue. The software application may further monitor the temperature rise and decay at the temperature probe. Based on the measured distance, the time and temperature data, and other relevant data, the software application calculates whether the nerve was properly ablated to kill the nerve. In some embodiments, the software application calculates the probability that the nerve was properly ablated to kill the nerve and displays the probability on a display device.

To provide for quick interaction with the user interface, the surgeon may select (e.g., click on) representations of a probe, a nerve, and one or more thermocouple needles, and arrange them in a virtual map displayed on a display device. The virtual map may be a cartoon-like map. The surgeon may click a start button and may start placing thermocouple needles in the virtual map, which may appear like the diagrams of FIGS. 7D and 7E, for example. The user interface may also display the active and passive areas of the ablation zone based on an RF energy level and allow the surgeon to change the RF energy level that is delivered to the target tissue in order to plan for an ablation procedure. After completing an ablation, the surgeon may also confirm, by using the cooling method described above and a virtual display map showing the temperature profile, that a nerve or tumor is dead or is likely dead. Then, the surgeon may work on ablating the next nerve or tumor.

In embodiments, a colored box or indicator may be displayed on a channel of the microwave generator indicating whether a nerve was properly ablated. For example, a green indicator may indicate that the nerve was properly ablated and a yellow indicator may indicate that the nerve was not properly ablated and that the ablation should be repeated.

In embodiments, the ablation needle or probe is first placed in tissue and then the temperature probe is placed in the tissue. In embodiments, the ablation probe may first be placed in tissue and then an imaging modality, e.g., fluoroscopy, X-ray, or computed tomography (CT), may be used to obtain an image of the placed ablation probe with respect to the bone and the nerve. A user interface may display the image and identify or indicate in the image where the remote temperature probe should be placed so that the surgeon, for example, can place the remote temperature probe within a certain distance of the ablation probe or the nerve to improve accuracy. The user interface may recommend where to place the remote temperature probe, e.g., within a couple of centimeters of the liver.

In embodiments, the controller 24 of FIG. 1B may execute a software application that determines that the nerves are likely at a particular location and that single-point thermometry works properly when within some window. The software application may then tell or show the surgeon the location of the window. In some embodiments, the software application may instruct the surgeon to place the remote temperature probe, may cause the generator to supply a small amount of RF energy to the ablation probe, and may determine whether the remote temperature probe senses a temperature change. If the software application determines that the remote temperature probe does not sense a temperature change or a large enough temperature change, the software application may give further instruct the surgeon to place the remote temperature probe at another location.

Prior to performing the ablative portion of the procedure, the surgeon may confirm or determine the location of a nerve by placing a needle at the probable location of the nerve and delivering a diagnostic block, e.g., an anesthetic or a fast-acting anesthetic. If the surgeon successfully blocks the nerve, the surgeon knows at least the approximate location of the nerve. The surgeon may provide only enough diagnostic block that gives a high degree of confidence that the needle was placed at or near the nerve. Then, the surgeon places the ablation probe at the same location as the needle used to deliver the diagnostic block in relation to the bony landmarks. Alternatively, the diagnostic block may be delivered to target tissue, and after a predetermined number days if the patient's pain goes away, an ablation procedure would be performed on the patient. The surgeon then places the ablation probe at the same location where the diagnostic block was delivered to the target tissue. The surgeon may place the ablation probe in the same anatomical reference location.

In some cases, the surgeon may deliver too much diagnostic block, which may flood an area and make it difficult to determine the location of the nerve. In some embodiments, a conductive diagnostic block is delivered to the nerve. If the conductive diagnostic block is successfully working on the nerve, the surgeon can ablate only where the conductive diagnostic block is located. The diagnostic block may include a fast-acting anesthetic, e.g., lidocaine. In some embodiments, an ablation procedure may be approved once there is a successful diagnostic block. Thus, approval may be obtained soon after delivery of the diagnostic block, thus improving efficiency by, for example, reducing a two-day procedure to a one-day procedure.

In embodiments, a thermal fluid may be used. The thermal fluid may be a high impedance thermal fluid or a fluid to which the surgeon can apply energy. The thermal fluid may include the diagnostic block and/or a contrast agent.

In embodiments, a company can certify an ablation procedure if certain certification thresholds are met and can indicate that the company will give away free ablation electrodes if the ablation procedure fails. One of the certification thresholds may be not to place more than a predetermined amount of diagnostic block.

If the surgeon places the contrast and the surgeon knows where the contrast went, the surgeon can target it again and confirm. That may guide the surgeon to where the surgeon places or brackets the temperature probe. The surgeon may put it on the other side of the contrast. The surgeon may drop contrast out of the ablation probe. The surgeon may place the ablation probe, drop contrast, and confirm that it goes to the same place. The contrast or contrast agents may be thermally reactive so that the surgeon can see the contrast or contrast agents on an imaging modality such as fluoroscopy. With the contrast agent in place, the surgeon may ablate and the contrast agent changes its imaging properties so it is no longer the fluid. The surgeon may be able to visualize the contrast agent or not visualize the contrast agent when all the contrast or contrast agent cooks off. In embodiments, liposomes that are leaky may be used instead of the contrast agent. A contrast agent may be put within the liposomes and at certain temperatures the contrast agent will leak out of the liposomes.

In embodiments, the various methods and features set forth in this disclosure may be tied to certification of a procedure. If the surgeon uses any or a subset of various features, then the procedure incorporating those features becomes certified. For example, if the surgeon uses any or a subset of the various features and use of the ablation probe results in a green light (indicating that the nerve was killed), but the patient still feels pain afterwards, then the company supplying ablation probes to the surgeon may give ablation probes to the surgeon free of charge.

If there are blood vessels above and below and there is rapid cooling, the surgeon may not know the direction of that cooling and how it is happening without the remote temperature probe. And the surgeon may not be able to see those blood vessels in imaging. In this scenario, the method may include monitoring temperature decay and the temperature throughout the procedure. This reduces the monitoring problem from a three-dimensional problem to a one-dimensional or two-dimensional problem. In some embodiments, a surgeon may use a fluoroscopy imaging modality to navigate to the ablation site. For example, a 90° swing on the C-arm may be employed. The surgeon may employ three-dimensional imaging from top to bottom and from side to side.

In embodiments, a surgeon may input the location or approximate location of a target nerve or target nerves and the location of anatomical features to a user interface. That information may then be processed to determine whether or not there has been a successful ablation. The user interface may present a graphical depiction of the anatomy and the surgeon may place the needle based on the graphical depiction. The user interface may present longitudinal data that shows where the needle was placed previously without a successful ablation. The data presented by the user interface may include the location, the amount of energy, and the amount of time.

There are a variety approaches to nerve ablation. In some embodiments, a monopolar probe obtains temperature information, either a temperature increase or a temperature decay, to understand what the heat sink environment looks like. In other embodiments, a remote temperature probe or needle is used to obtain temperature information. The temperature information may include temperature curves that give an indication of successful ablation at certain distances.

In embodiments, a bipolar instrument is used. A plane may be defined between the two poles of the bipolar instrument and energy largely flows in the plane between the two poles. Thus, there is a high probability of complete ablation along the plane between the two poles because there is consistency in where the nerve comes out of the bone that the surgeon is bracketing. The cooling curves may work well in the bipolar case because there will be two cooling curves and if the ablation worked the tissue should cool differently.

The monopolar temperature monitoring may be linked to the bipolar temperature monitoring and the remote temperature monitoring. The temperature curves may be overlaid on each other. Also, temperature curves may be compared to each other to determine information about the ablation. For example, if one temperature curve is different from another temperature curve, the ablation was probably not successful at killing the nerve. If two temperature curves are consistent with each other and are consistent with temperature curves of other ablations, the ablation was probably successful at killing the nerve.

Figure 8:
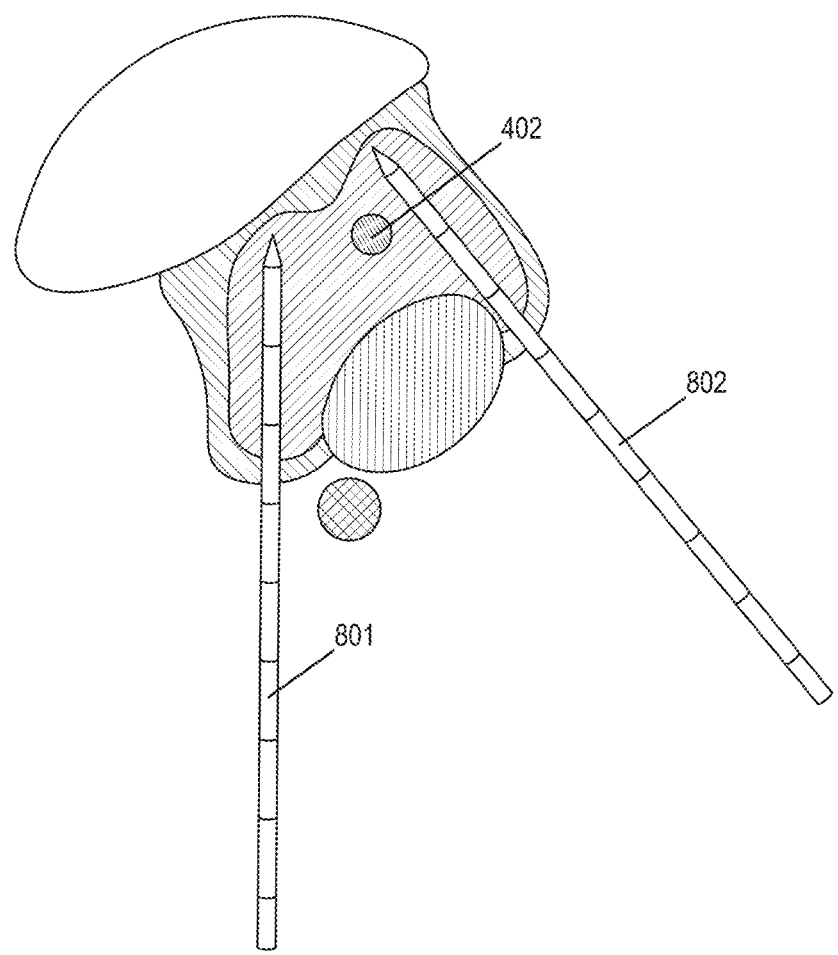
FIG. 8 is a diagram illustrating the use of bipolar probes to ablate target tissue according to embodiments of this disclosure.

In the bipolar mode illustrated in FIG. 8, the temperature of the return electrode generally does not exceed about 100° C. depending on whether the return electrode is cooled. The return electrode is symmetric with the active electrode and there are balanced thermal decay curves. If a temperature curve is very different from another temperature curve, then the ablation may not be in the expected or desired plane. In some cases, there may be a relationship between the roll-offs of the temperature curves for the bipolar configuration because the energy delivery is passive. However, there may not be symmetry between the temperature curves for the bipolar configuration.

In some cases, a clinician places multiple ablation electrodes one after another along the spine and uses an RF system to control delivery of energy to the multiple ablation electrodes. Thus, as the clinician places one ablation probe, the clinician can start an ablation and begin placing another ablation probe. In embodiments, the monitoring of temperature decay to determine the success of ablation may be interweaved with energy delivery to subsequent electrodes to improve the efficiency of ablation procedures.

Aspects of this disclosure may be applied to bipolar ablation electrodes. If two monopolar ablation electrodes are operating near each other, a thermal insulator may be formed between the ablation electrodes because heat will not be conducted from one active ablation zone to another active ablation zone. However, as illustrated in FIG. 8, the surgeon brackets the facet joint where the nerve comes out of the bone, places two bipolar electrodes 801, 802, and causes RF energy to be transmitted from one electrode 801 to the next electrode 802. The temperature curves of both electrodes 801, 802 may not cool as fast as using only one electrode because no energy crosses the symmetric line between the active ablation zones of the electrodes 801, 802.

Bipolar tools may have slightly smaller ablation areas than monopolar tools. This may be because there is one resistor building around the energy delivery site for monopolar instead of two resistors for bipolar. The window of opportunity is smaller. If there are two cooled electrodes of similar geometry, they have similar impedance and thus there is twice the impedance. In bipolar tools, the current may be conducted in a specific pattern. The window is smaller, but there is a lot more focus in the energy so the clinician can be sure that energy is being provided between the two electrodes. The advantage of bipolar is the surgeon can bracket the known location of the nerve rather than trying to pinpoint with one electrode to get the nerve.

In embodiments, the distance between two electrodes or two probes may be part of a certification process. The methods of this disclosure may depend on that distance and may set a window for that distance. A user interface may allow a clinician to select the suspected locations of the ablation probes, the nerve or other target tissue, and the remote temperature probes or thermocouples. In embodiments, the thermocouples may be low temperature thermocouples or high temperature thermocouples.

As shown in FIGS. 7D and 7E, the nerve 402 is somewhere between the remote temperature probe or thermocouple 725 and the ablation probe 105, and the temperature at the nerve location needs to be high enough to kill the nerve 402. Even when the ablation electrode 105 is cooled and its temperature is unknown or is cool, the temperatures at other locations can be assumed. For example, because the temperature decay curve may exhibit a logarithmic decay, one can assume a distant initial temperature. Also, one can assume the temperature near the ablation probe 105 is about 100° C. because the RF energy is limited to about 100° C. at which water boils and there is no longer conductivity to allow the RF energy to conduct through tissue. For a cool tip, once cycling starts, the temperature is about 100° C. about four millimeters away from the ablation electrode. And one can assume that the temperature on the ablation electrode surface is generally repeatable based upon energy delivery. Using the assumed temperatures and the temperature measured by the remote temperature probe, one can determine information about the temperature between those three locations including the approximate temperature at the nerve.

In embodiments, the RF energy may be pulsed to obtain information including temperature information. The pulsed RF energy may be used to confirm that the RF energy has reached the remote temperature probe 725. The remote temperature probe 725 may be used to monitor the growth and decay of the temperature in response to the pulsed RF energy. In this way, non-therapeutic energy is delivered to determine whether an ablation procedure is going to fail without ablating the tissue. Otherwise, unsuccessful ablation of the nerve may create more scar tissue. Also, the unsuccessful ablation of the nerve may cause a singing effect and create more pain.

In embodiments, cooling may first be performed or a quick ping of RF energy may be delivered by the ablation probe 105 for a short period of time, e.g., five seconds, which does not cause a significant amount of damage. Then, the remote temperature probe 725 may be used to confirm that the ablation probe 105 and the remote temperature probe 725 are in thermal communication with each other.

Embodiments of this disclosure may be used to obtain information about the thermal environment before, during, and after the ablation procedure. In embodiments, systems and methods of this disclosure may determine the content of the tissue between the ablation electrode 105 and the remote temperature probe 725 using information obtained from the pinging and/or pulsing of RF energy. If the tissue is conductive, the remote temperature probe 725 may detect a temperature and/or a temperature difference quickly. If, on the other hand, there is an insulator between the ablation electrode 105 and the remote temperature probe 725, the remote temperature probe 725 may not sense a temperature, depending on the sensitivity of the remote temperature probe 725.

In embodiments, a thermal conductivity contour may be auto-populated on a display screen of a user interface. The systems and methods of this disclosure may use this information for power and duration calculations. For example, this information could be used for controlling the amount of power delivered to the ablation probe 105 or target tissue.

Figure 9:
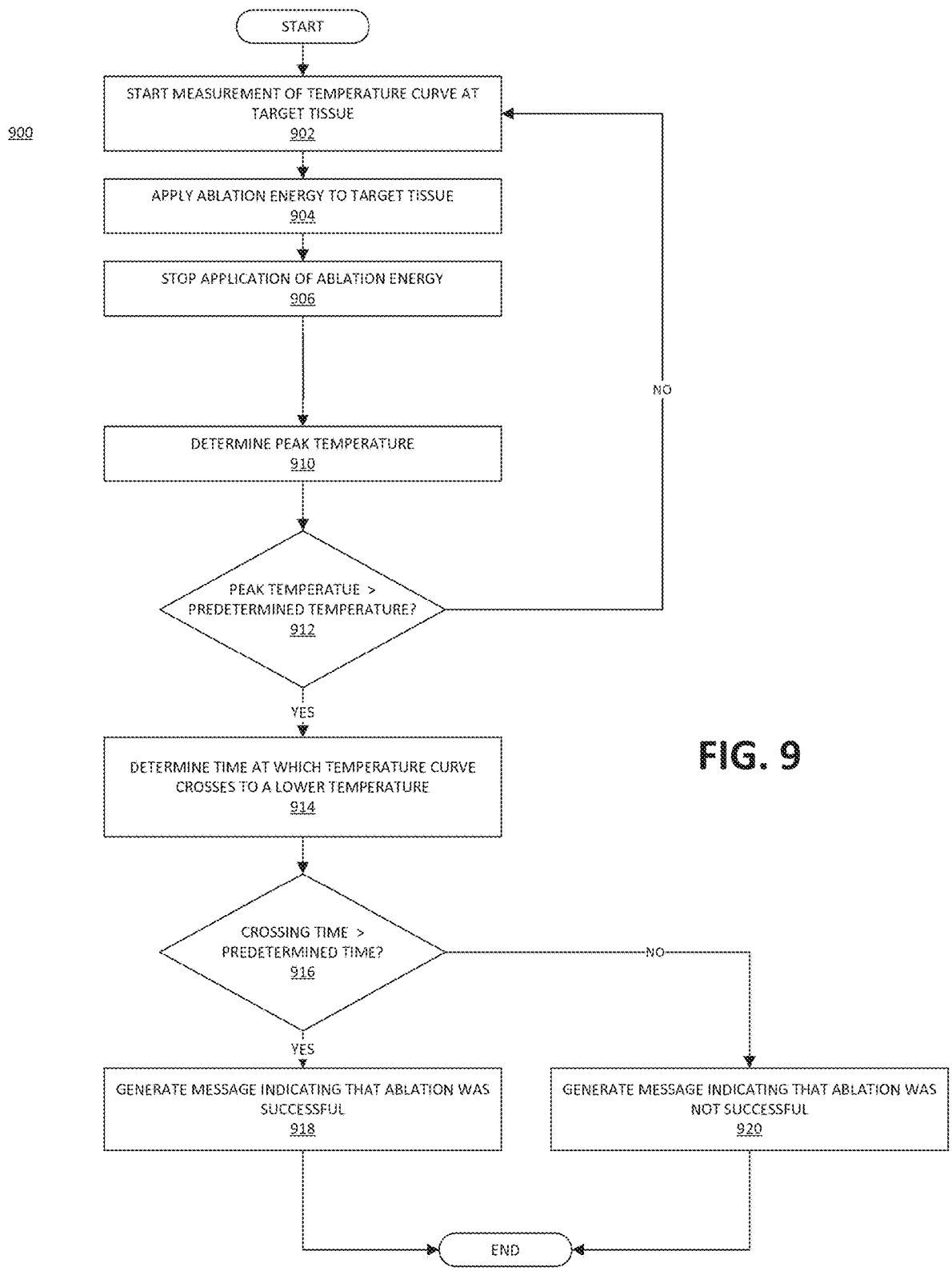
FIGS. 9 and 10 are flowcharts illustrating methods of detecting successful ablation of target tissue according to embodiments of this disclosure.

FIG. 9 is a flowchart illustrating a method 900 of detecting successful ablation of target tissue according to embodiments. First, the measurement of a temperature curve at target tissue is started (block 902). Ablation energy is then applied to the target tissue (block 904) for a period, after which the application of ablation energy is stopped (block 906). Next, the temperature curve is analyzed to determine a peak temperature (block 910). Next, it is determined whether the peak temperature is greater than a predetermined temperature (block 912). If the peak temperature is not greater than the predetermined temperature, the method repeats block 902 through block 912.

If the peak temperature is greater than the predetermined temperature, the method 900 further includes determining a time at which the temperature curve crosses to a lower temperature (block 914). If the crossing time is greater than a predetermined time (block 916), which is a time corresponding to a time at which the ablation would be successful, a message indicating that the ablation was successful is generated (block 918). If, on the other hand, the crossing time is not greater than the predetermined time, a message indicating that the ablation was not successful is generated (block 920). This message may cause the surgeon to attempt to ablate the target tissue again at a different location, for example.

Figure 10:
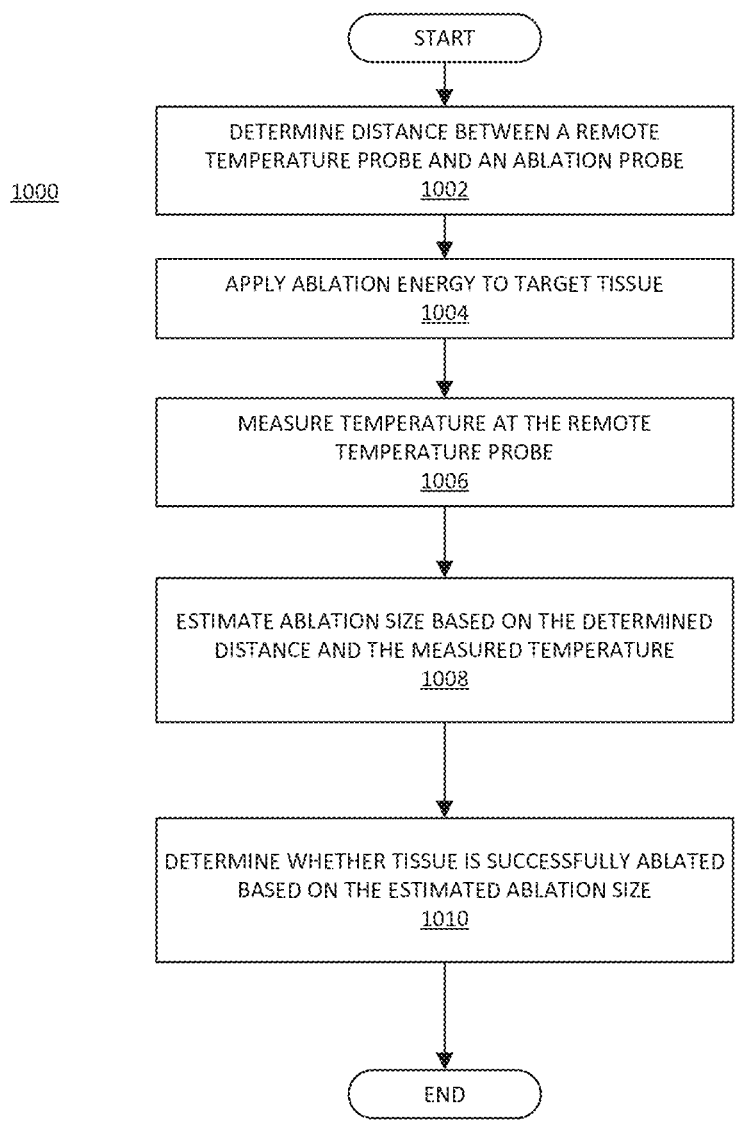

FIG. 10 is a flowchart illustrating another method 1000 of detecting successful ablation of target tissue according to other embodiments. First, a distance between a remote temperature probe and an ablation probe is determined (block 1002). In embodiments, the determined distance is between about 1.0 cm and about 2.0 cm and the surgeon places the remote temperature probe in tissue according to the determined distance. For example, if the determined distance is 1.5 cm, the surgeon places the remote temperature probe 1.5 cm away from the ablation probe.

Next, the temperature at the remote temperature probe is measured (block 1006) and the ablation size is estimated based on the determined distance and the measured temperature (block 1008). As described above, the ablation size may be estimated by: (1) interpolating between the measured temperature, an assumed temperature near the ablation electrode, and an assumed initial temperature remote from the ablation electrode to obtain temperature values, (2) evaluating an Arrhenius integral equation using the obtained temperature values, and (3) determining ablation size based on a result of evaluating the Arrhenius integral equation. Then, it is determined whether the tissue is successfully ablated based on the estimated ablation size (block 1010). Determining whether the target tissue is successfully ablated may include determining whether the estimated ablation size includes or encompasses the target tissue.

Figure 11:
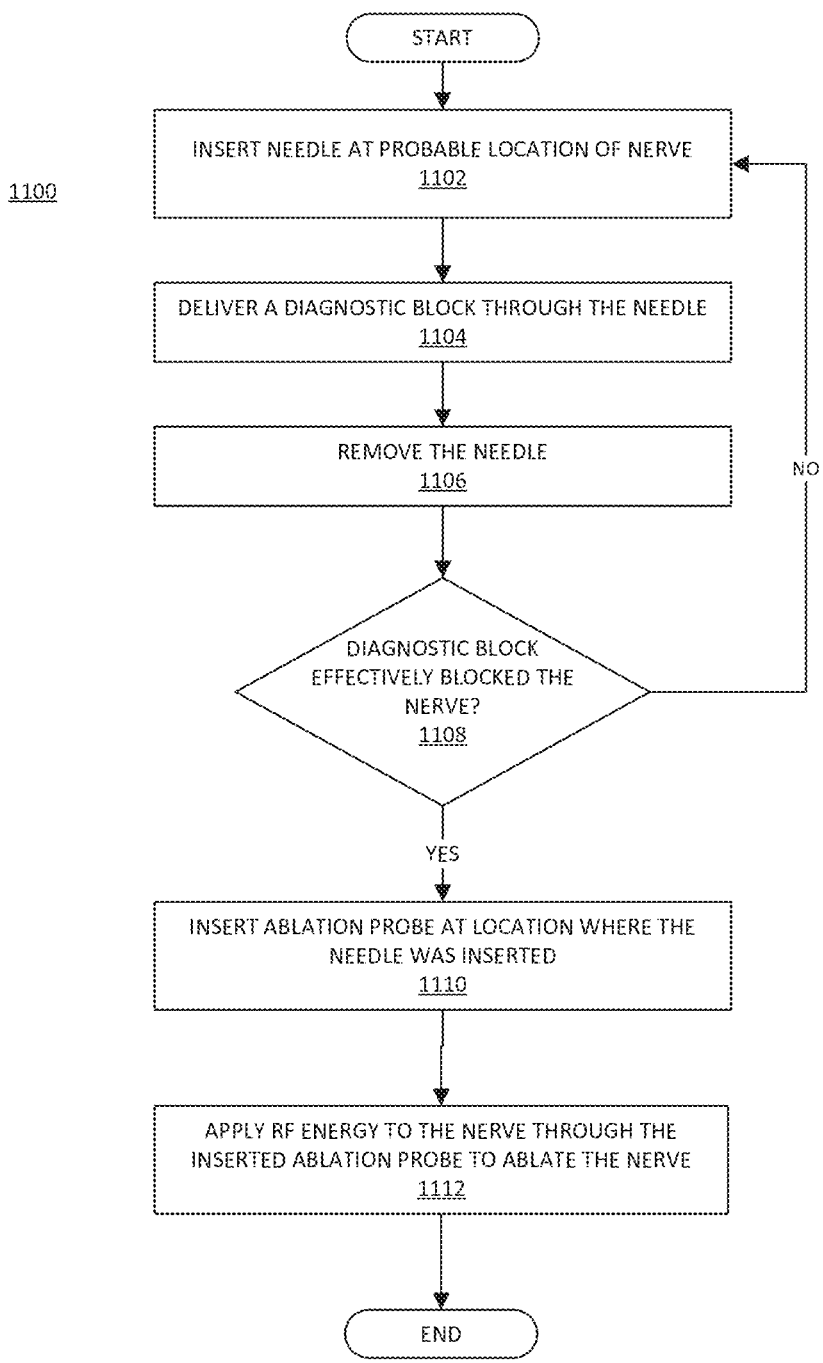
FIG. 11 is a flowchart illustrating a method of ablating nerve tissue according to embodiments of this disclosure.

FIG. 11 is a flowchart illustrating a method 1100 of ablating tissue, e.g., a nerve, according to embodiments. First, a needle is inserted at the probable location of a nerve (block 1102). A diagnostic block is then delivered through the needle (block 1104) and the needle is removed (block 1106). Delivering the diagnostic block may include delivering a sufficient amount of diagnostic block to effectively block the nerve, but delivering less than an amount that would flood the tissue and make it difficult to accurately locate the nerve. The diagnostic block may be an anesthetic, a fast-acting anesthetic, or lidocaine. Next, it is determined whether the diagnostic block effectively blocked the nerve (block 1108). If the diagnostic block did not effectively block the nerve, the needle may be placed at another probable location of the nerve and the method 1100 repeats block 1102 through block 1108.

If the diagnostic block effectively blocked the nerve, the method 1100 includes inserting an ablation probe at the location where the needle was inserted (block 1110) and applying RF energy to the nerve through the inserted ablation probe to ablate the nerve (block 1112).

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

The invention claimed is:

1. A method, comprising:
   applying, by an ablation electrode, ablation energy at target tissue;
   cooling the ablation electrode;
   measuring a temperature curve generated at the target tissue in response to the application of the ablation energy at the target tissue;
   determining a time at which the temperature curve crosses to a temperature lower than a predetermined peak temperature on the temperature curve; and
   determining whether or not the target tissue was successfully ablated based on the temperature curve.

2. The method of claim 1, further comprising, if it is determined that the target tissue was not successfully ablated, issuing a message indicating that the target tissue was not successfully ablated.

3. The method of claim 1, further comprising determining a peak temperature on the temperature curve.

4. The method of claim 3, further comprising determining whether the peak temperature is greater than the predetermined peak temperature.

5. The method of claim 1, further comprising issuing a message indicating that the target tissue was successfully ablated if the determined time is greater than a predetermined time.

6. A system, comprising:
   a radio frequency (RF) generator configured to generate RF energy;
   an ablation instrument configured to deliver the RF energy to target tissue to ablate the target tissue;
   a cooling fluid pump configured to pump cooling fluid to the ablation instrument;
   a temperature sensor configured to measure temperature at the target tissue; and
   a controller configured to:
   control the RF generator to supply the RF energy to the ablation instrument;
   control the cooling fluid pump to pump cooling fluid to the ablation instrument;
   measure a temperature curve generated at the target tissue in response to the delivery of the RF energy to the target tissue;
   determine a time at which the temperature curve crosses to a temperature lower than a predetermined peak temperature on the temperature curve;
   determine whether the target tissue was successfully ablated based on the temperature curve.

7. The system of claim 6, wherein the controller is further configured to, if it is determined that the target tissue was not successfully ablated, issue a message indicating that the target tissue was not successfully ablated.

8. The system of claim 6, wherein the controller is further configured to control the temperature sensor to measure the temperature curve at the target tissue.

9. The system of claim 6, wherein the controller is further configured to determine a peak temperature on the temperature curve.

10. The system of claim 9, wherein the controller is further configured to determine whether the peak temperature is greater than the predetermined peak temperature.

11. The system of claim 6, wherein the controller is further configured to issue a message indicating that the target tissue was successfully ablated if the determined time is greater than a predetermined time.

12. The system of claim 6, wherein the temperature sensor is disposed on the ablation instrument.

13. A system, comprising:
   an ablation instrument configured to deliver ablation energy to target tissue to ablate the target tissue;
   a cooling fluid pump configured to pump cooling fluid to the ablation device;
   a temperature sensor configured to measure temperature at the target tissue; and
   a controller configured to:
   control the ablation device to deliver the ablation energy to the target tissue;
   control the cooling fluid pump to pump cooling fluid to the ablation device;
   control the temperature sensor to measure a temperature curve generated at the target tissue in response to the delivery of ablation energy to the target tissue;
   determine a time at which the temperature curve crosses to a temperature lower than a predetermined peak temperature;
   compare the determined time to a predetermined time;
   determine whether or not the target tissue was successfully ablated based on the comparison; and
   generate an indication of whether or not the target tissue was successfully ablated.

14. The system of claim 13, wherein the controller is further configured to generate an indication that the target tissue was not successfully ablated in response to a determination that the target tissue was not successfully ablated.

15. The system of claim 14, wherein the controller is further configured to determine whether the peak temperature is greater than the predetermined peak temperature.

16. The system of claim 13, wherein the controller is further configured to determine a peak temperature on the temperature curve.

17. The system of claim 13, wherein the controller is further configured to issue a message indicating that the target tissue was successfully ablated if the determined time is greater than the predetermined time.

18. The system of claim 13, wherein the temperature sensor is disposed on the ablation instrument.

* * * * *